United States Patent
Di Giacomo et al.

(10) Patent No.: US 8,728,131 B2
(45) Date of Patent: May 20, 2014

(54) WEDGED PROFILE PLATE

(75) Inventors: Giovanni Di Giacomo, Rome (IT); Alberto Constantini, Rome (IT)

(73) Assignee: Arthrex, Inc., Naples, FL (US)

( * ) Notice: Subject to any disclaimer, the term of this patent is extended or adjusted under 35 U.S.C. 154(b) by 940 days.

(21) Appl. No.: 12/489,300

(22) Filed: Jun. 22, 2009

(65) Prior Publication Data
US 2009/0318977 A1    Dec. 24, 2009

Related U.S. Application Data (60) Provisional application No. 61/167,808, filed on Apr. 8, 2009, provisional application No. 61/074,528, filed on Jun. 20, 2008.

(51) Int. Cl.
*A61B 17/80* (2006.01)

(52) U.S. Cl.
USPC ............................................. 606/297

(58) Field of Classification Search
USPC .................. 606/75, 280, 325, 329, 281–284, 606/286–299
See application file for complete search history.

(56) References Cited

U.S. PATENT DOCUMENTS

| | | | | |
|---|---|---|---|---|
| 5,352,229 A * | 10/1994 | Goble et al. | ................ | 606/75 |
| 5,690,629 A * | 11/1997 | Asher et al. | ................ | 606/75 |
| 6,336,928 B1 * | 1/2002 | Guerin et al. | ................ | 606/282 |
| 6,524,311 B2 * | 2/2003 | Gaines, Jr. | ................ | 606/278 |
| 6,533,787 B1 * | 3/2003 | Lenke et al. | ................ | 606/75 |
| 7,481,830 B2 * | 1/2009 | Wall et al. | ................ | 606/297 |
| 7,883,510 B2 * | 2/2011 | Kim et al. | ................ | 606/75 |
| 2002/0193795 A1 | 12/2002 | Gertzbein et al. | | |

FOREIGN PATENT DOCUMENTS

| | | |
|---|---|---|
| EP | 1 402 829 A2 | 3/2004 |
| WO | WO 01/56489 A1 | 8/2001 |
| WO | WO 2006/025921 A2 | 3/2006 |
| WO | WO 2006/122194 A1 | 11/2006 |
| WO | WO 2007/134223 A2 | 11/2007 |

* cited by examiner

*Primary Examiner* — Michael T Schaper
*Assistant Examiner* — Michael Araj
(74) *Attorney, Agent, or Firm* — Dickstein Shapiro LLP (57) ABSTRACT

A bone plate used in conjunction with various procedures to correct certain deformities, such as a Latarjet procedure. The bone plate is provided with a plurality of spikes having a truncated, pyramidal shape with a plurality of sides or faces that converge to a tip line. The height of each spike is of about 2.5 to about 3 mm. The design of the spikes allows the plate to stay in the right position by simply pressing the plate with the fingers on the bone or using a specific instrument (before the fixation holes are drilled and the fixation devices such as screws are secured). The bone plate may be provided with side, lateral faces that have a non-uniform width (i.e., a wedged profile) to allow for orthograde placement of the fixation device, even in the case of angled bone surfaces.

26 Claims, 12 Drawing Sheets

WEDGED PROFILE PLATE

CROSS-REFERENCE TO RELATED APPLICATIONS

This application claims the benefit of U.S. Provisional Application No. 61/167,808, filed Apr. 8, 2009, and of U.S. Provisional Application No. 61/074,528, filed Jun. 20, 2008, the entire disclosures of both of which are incorporated by reference herein.

BACKGROUND OF THE INVENTION

1. Field of the Invention

The present invention relates to a novel bone plate.

2. Description of the Related Art

Osteotomies are procedures that surgically reorient the alignment of a deformed bone. The aim of an osteotomy is to realign the bearing surfaces of a joint to allow normal areas to articulate, moving abnormal areas away from the load-bearing axis.

Figure 1:
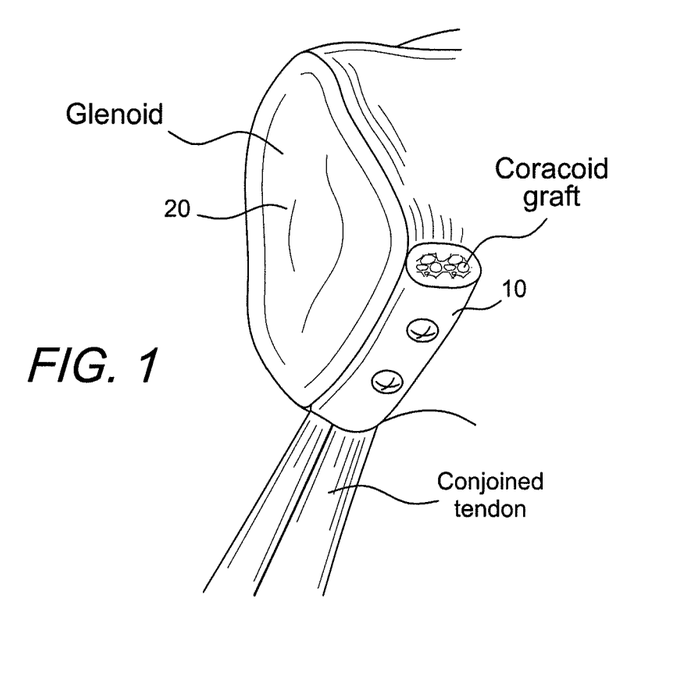
FIGS. 1 and 2 illustrate a perspective view and a cross-sectional view, respectively, of a coracoid process secured with screws during a conventional Latarjet procedure.
Figure 2:
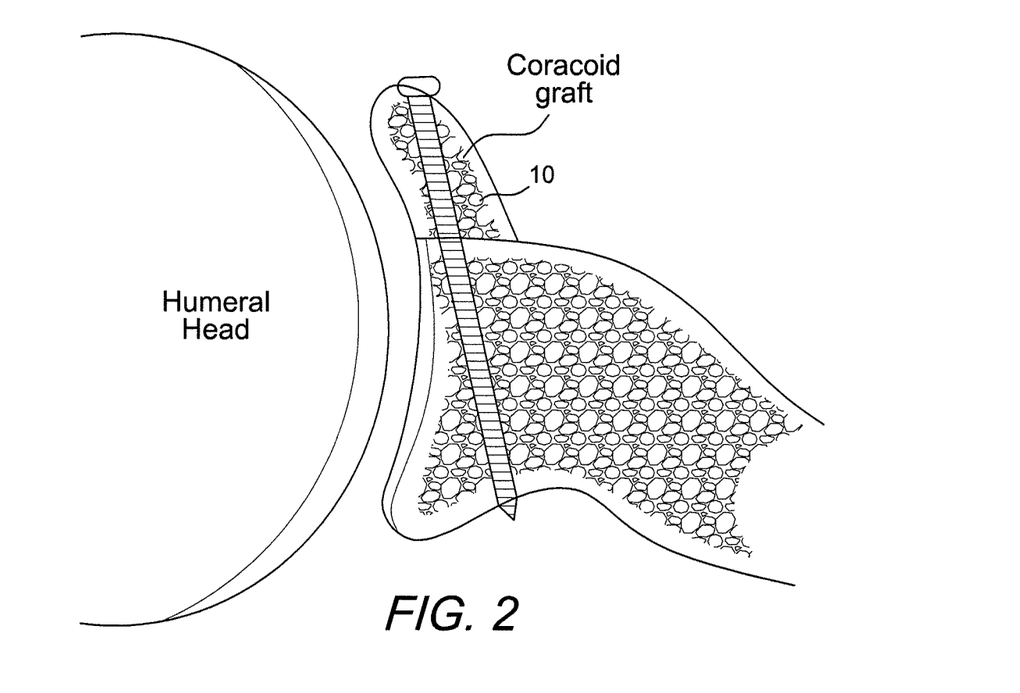

The Latarjet procedure is known in the art and describes the coracoid bone block procedure. French surgeon Michel Latarjet first suggested that the horizontal limb of the coracoid process be fixed with a screw flush to the anteroinferior margin of the glenoid, making a horizontal incision through the fibers of the subscapularis. FIGS. 1 and 2 illustrate the attachment of the coracoid process 10 to the glenoid edge 20, to reduce instability during the Latarjet procedure. Although the Latarjet procedure has been constantly improved since 1954, there remains always a danger that the coracoid process may break apart as a result of various factors such as: (i) the screws being screwed too tightly during the procedure; and/or (ii) medial necrosis of the bone graft due to altered bone-to-bone integration, caused by insufficient mechanical compression, already present in the bone fixation phase.

The coracoid breakage (i.e., medial necrosis of the bone graft) is explained by the intrinsic difficulty of the Latarj et technique, which entails the fixation of the coracoid on the "steep" neck of the scapula. To obtain a valid match between coracoid and glenoid, the two lag screws must be introduced perpendicular to the neck of the scapula; this step is sometimes made difficult by the small and deep surgical approach, thereby preventing perfect orientation of drill and screwdriver, and increasing anyway the possibility of intra-articular protrusion of the screws.

Accordingly, there is a need for better compression and load distribution between the two bone surfaces (neck of the scapula and coracoid) during a Latarjet procedure. A mini-plate with a shape better suited to the mechanical and biological characteristics of the Latarjet technique, with improved results, is also needed. A bone plate that may be used in conjunction with a Latarjet procedure, as well as with other osteotomies to correct certain deformities, is needed.

SUMMARY OF THE INVENTION

The present invention provides a bone plate used in conjunction with various procedures to correct certain deformities (including a Latarjet procedure). The bone plate is provided with a plurality of spikes having a truncated, pyramidal shape with a plurality of sides or faces that converge to a tip line. The spikes allow the plate to stay in the right position by simply pressing the plate with the fingers or using a specific instrument on the bone (before the fixation holes are drilled and before the fixation devices such as screws are secured). The bone plate may be provided with side, lateral faces, at least one of them having a non-uniform width (i.e., a wedged profile) to allow for orthograde placement of the fixation device (for example, a screw) even in the case of angled bone surfaces.

Other features and advantages of the present invention will become apparent from the following description of the invention, which refers to the accompanying drawings.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a bone plate that may be used in conjunction with various procedures such as osteotomies, or bone block transplants, or small joint surgeries to correct certain deformities including a Latarjet procedure.

Referring now to the drawings, where like elements are designated by like reference numerals, FIGS. 3-10 illustrate embodiments of a bone plate 100, 200, 300, 400 that may be used in conjunction with osteotomies to correct certain deformities (including, among others, the Latarjet procedure).

Figure 3:
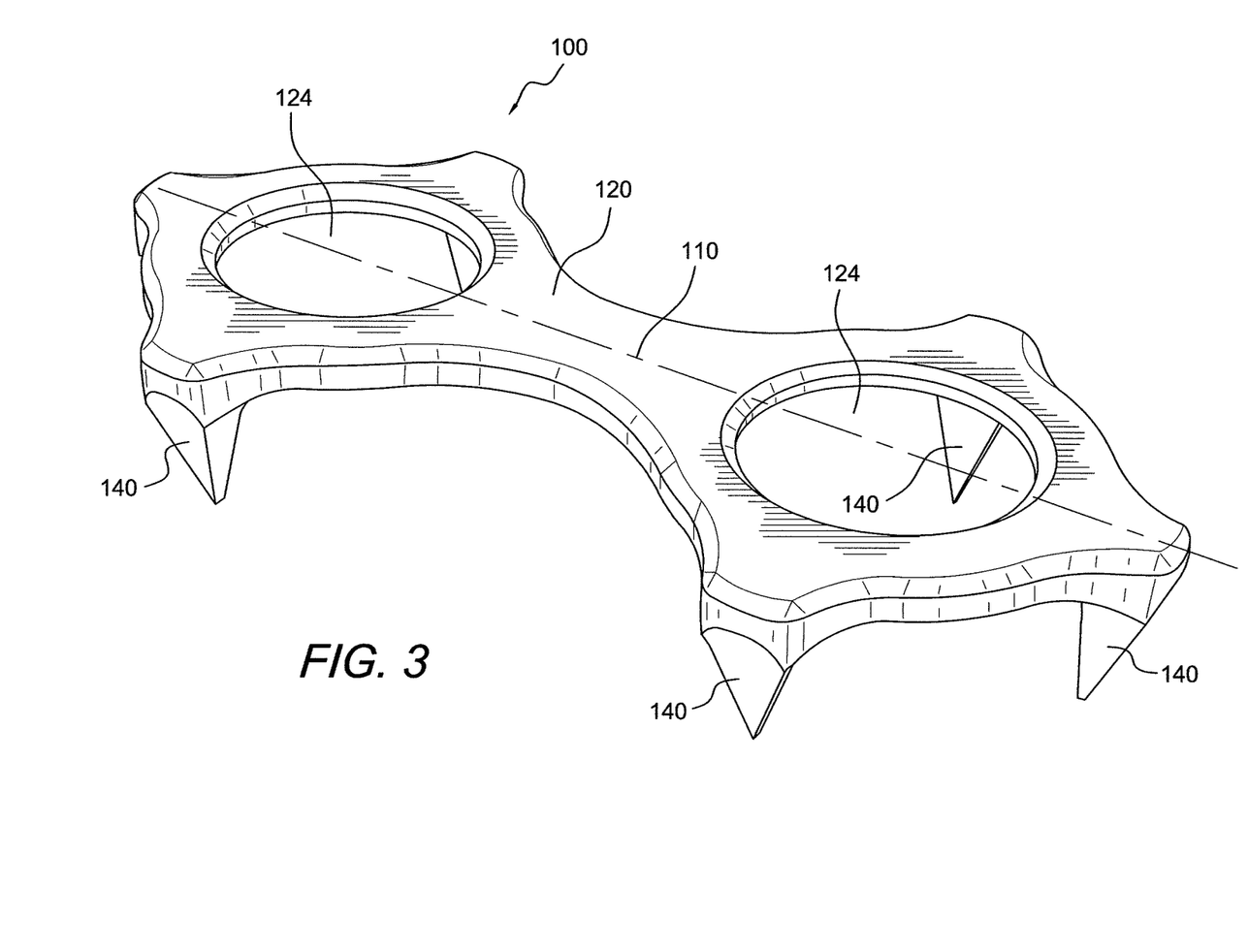
FIGS. 3-5 illustrate various views of a bone plate according to a first embodiment of the present invention.
Figure 4:
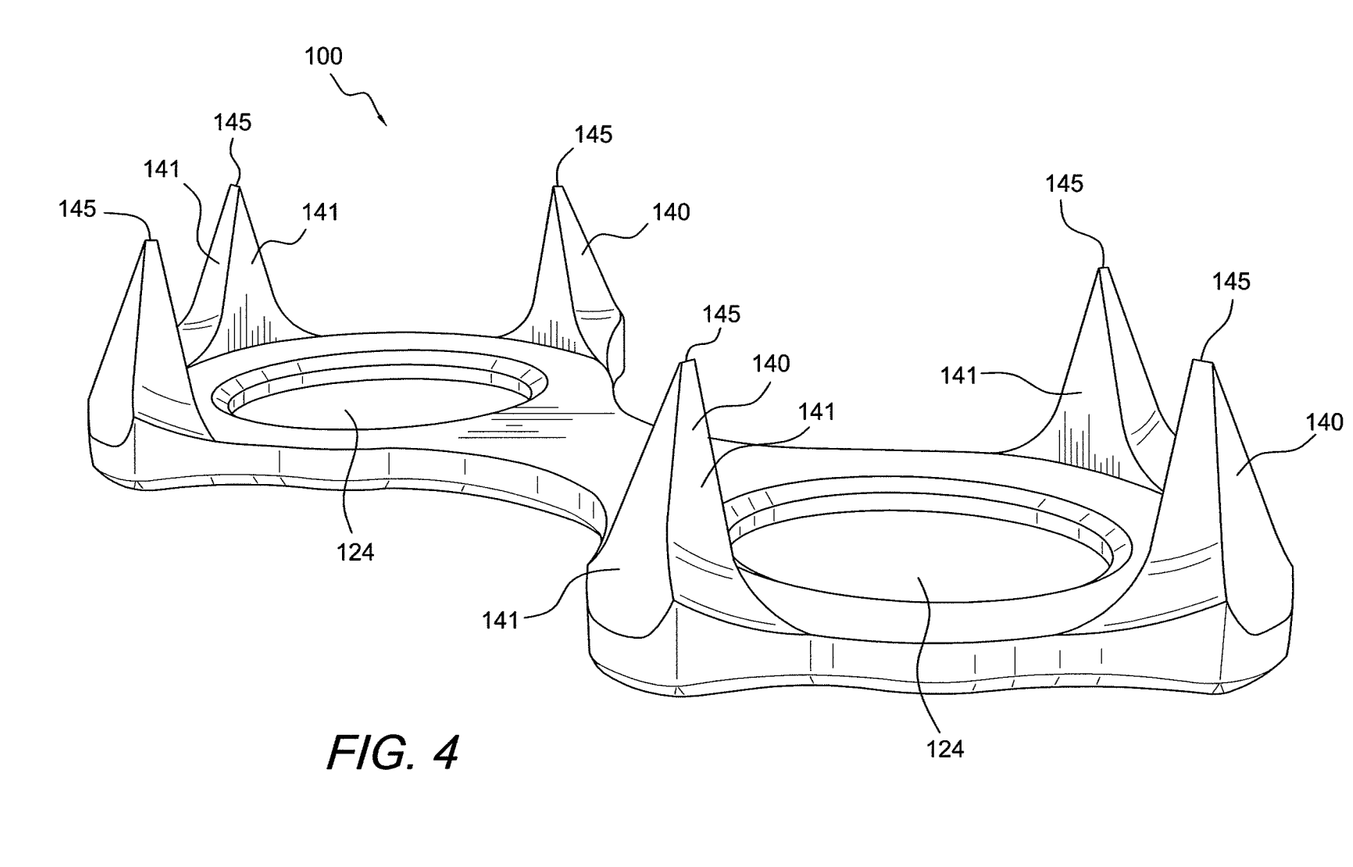
Figure 5A:
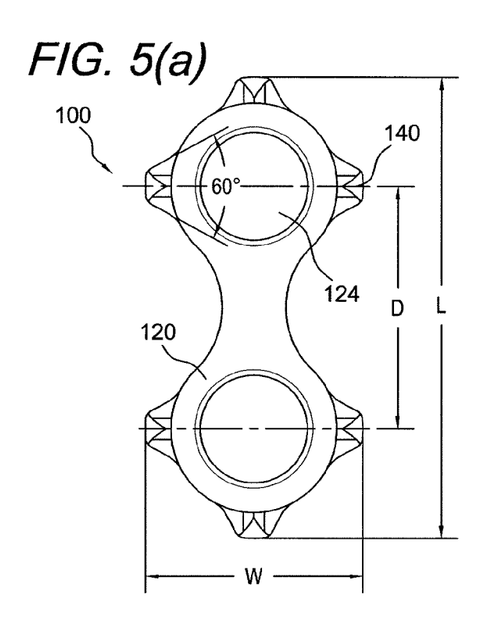
Figure 5B:
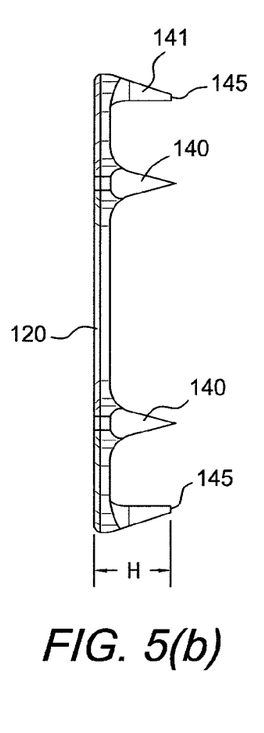

Bone plate 100 of the first embodiment of the present invention (shown in FIGS. 3-5) includes a rigid plate body 120 having an elongated "FIG. 8" configuration, as shown in FIG. 3, for example. As illustrated in FIG. 5a, and according to an exemplary embodiment of the invention, rigid body 120 has a length "L" of about 15 to 20 mm, more preferably of about 18 mm, and a width "W" of about 5 to about 10 mm, more preferably of about 6.5 mm.

Bone plate 100 is also provided with a plurality of small projecting teeth, protuberances or spikes 140. Projecting teeth or spikes 140 are designed to allow the plate 100 to stay in the right position (once the surgeon has pressed the plate with his/her fingers, or using a specific instrument, on the bone block) before the fixation holes are drilled and before the fixation devices (for example, screws) are secured. The exemplary embodiment illustrated in FIGS. 3-5 shows bone plate 100 provided with six spikes 140, two of the spikes being positioned on the longitudinal axis 110 of body 120. The remaining spikes 140 are located opposite each other and in symmetry relative to the longitudinal axis 110.

Figure 5C:
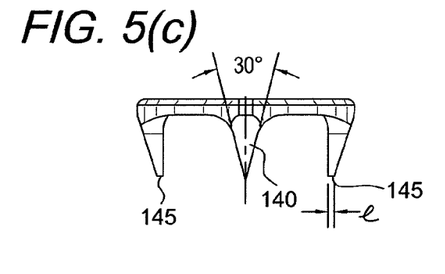
Figure 5D:
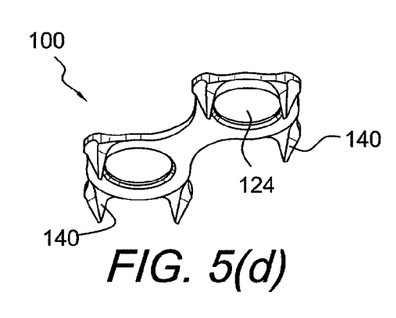
Figure 5E:
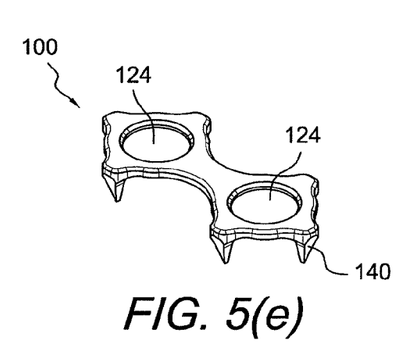

As shown in more detail in FIGS. 5a and 5c, spikes 140 have a truncated, pyramidal shape with a plurality of sides or faces 141 that converge to tip 145 (line 145) of each spike 140.

In an exemplary embodiment, each spikes includes four faces 141 that converge to tip 145. Tip 145 is preferably a thin line with a length "l" (FIG. 5c) of about 0.1 to 0.2 mm, more preferably of about 0.2 mm. The height "H" of each spike is of about 3 mm with the bone plate (FIG. 5b) or of about 2.5 mm without the bone plate.

Plate 100 is also provided with two openings 124 disposed about the longitudinal axis 110 of body 120. Openings 124 may be threaded and/or countersunk and are configured to receive fixation devices (such as two fixation devices used in conjunction with the Latarjet technique). In an exemplary embodiment, the distance "D" (FIG. 5a) between the two openings 124 is of about 10 mm, more preferably of about 9.5 mm.

Figure 6:
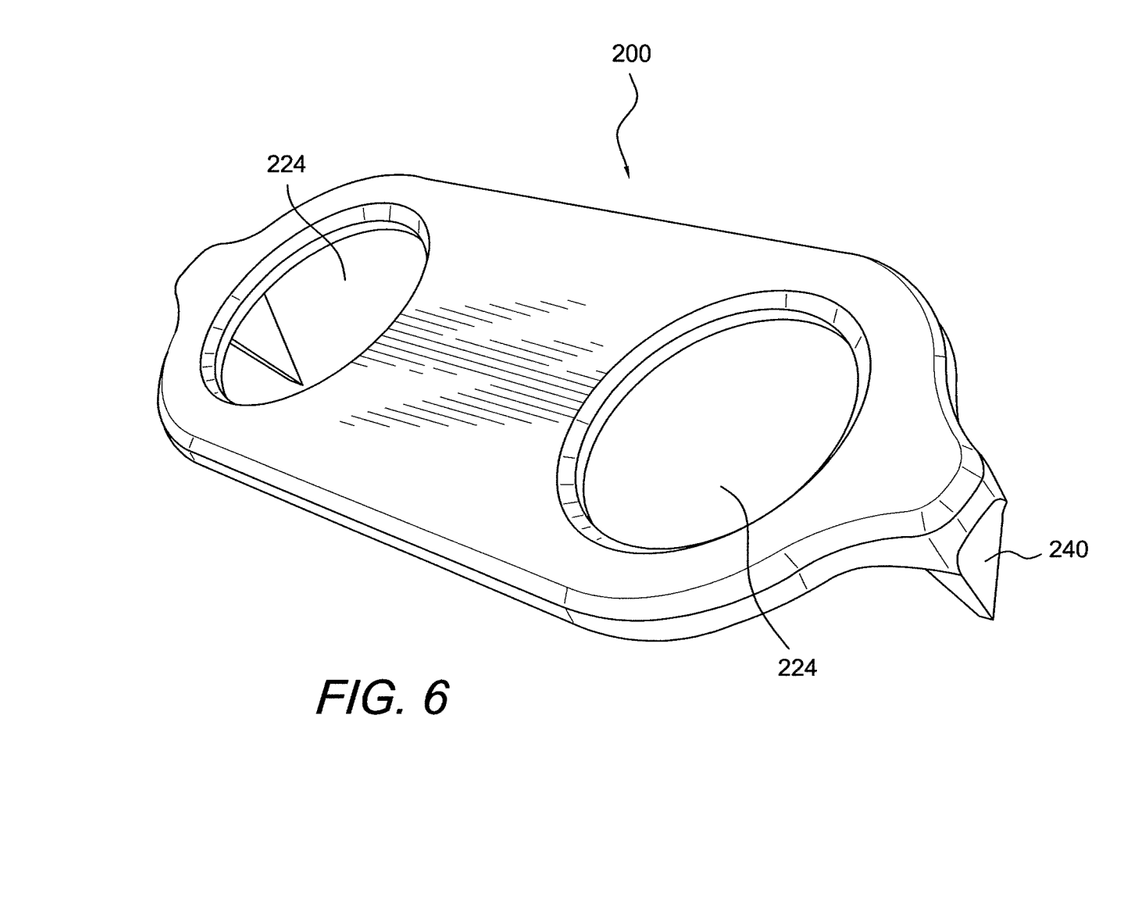
FIGS. 6-8 illustrate various views of a bone plate according to a second embodiment of the present invention.
Figure 7:
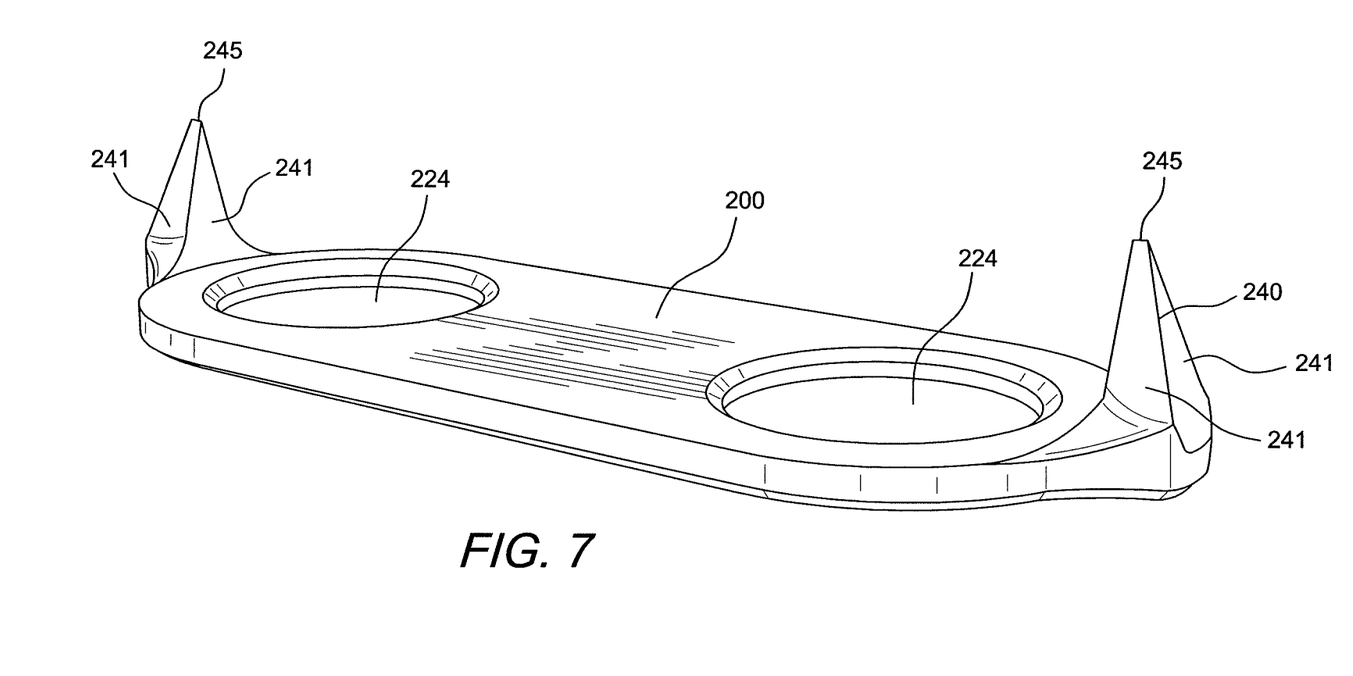
Figures 8A, 8C:
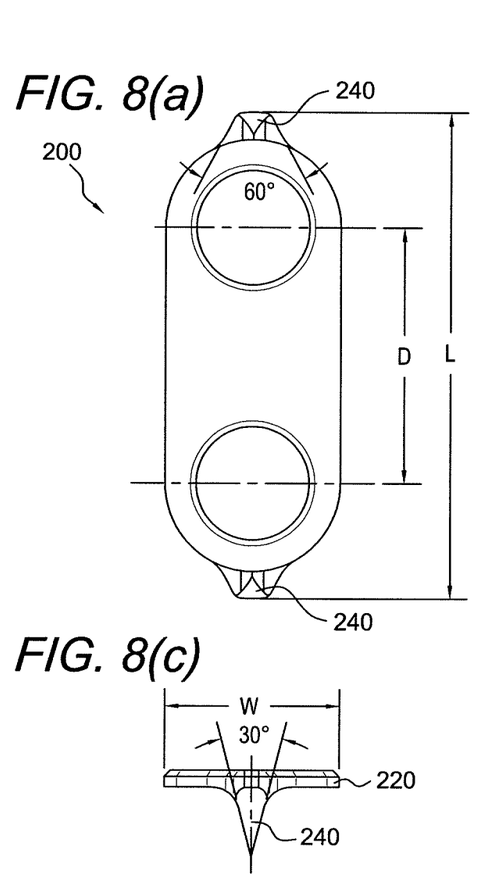
Figure 8B:
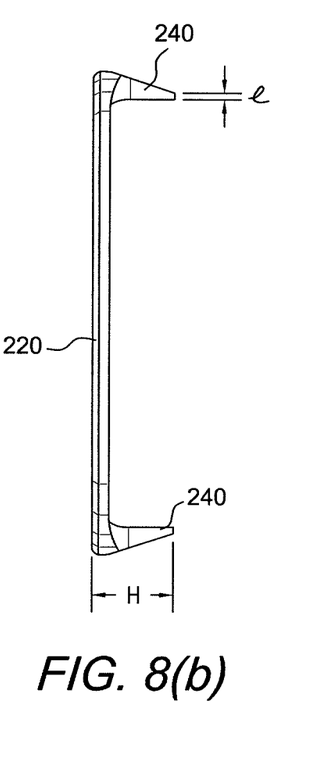
Figures 8D, 8E:
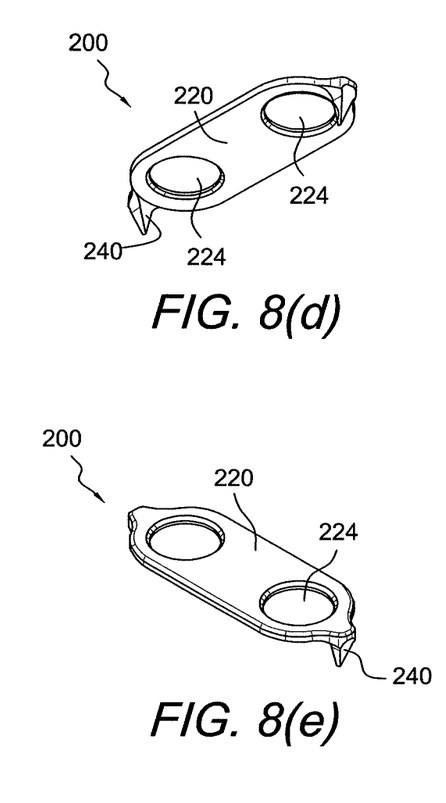

Bone plate 200 of the second embodiment of the present invention (shown in FIGS. 6-8) includes a rigid plate body 220 having an oval shape and provided with a plurality of small projecting teeth, protuberances or spikes 240 (two shown in FIGS. 6-8). Spikes 240 are similar to spikes 140 of plate 100 in that spikes 240 are also provided with a truncated, pyramidal shape, each spike terminating in tip 250 having a length "l" (FIG. 8b) of about 0.1 to 0.2 mm. The height "H" of each spike is of about 3 mm with the bone plate (FIG. 8b) or of about 2.5 mm (without the bone plate).

Body plate 220 is also provided with two openings 224 (that may be threaded and/or countersunk) configured to receive fixation devices (such as, for example, two fixation devices used for the Latarjet procedure). Projecting teeth or spikes 240 are designed to allow the plate 200 to stay in the right position (once the surgeon has pressed the plate with his/her fingers, or using a specific instrument, on the bone block) before the fixation holes are drilled and before the fixation devices (for example, screws) are secured.

Body 220 of the plate 200 has a length "L" (FIG. 8a) of about 15 to 20 mm, more preferably of about 18 mm, and a width "W" of about 5 to about 10 mm, more preferably of about 6.5 mm.

Bone plate 300 of the third embodiment of the present invention (shown in FIG. 9) has a wedged design (as opposed to the parallel design of FIG. 6, for example). The special profile of the plate 300 enables orthograde placement of the fixation device (for example, a screw) even in the case of angled bone surfaces.

Figure 9:
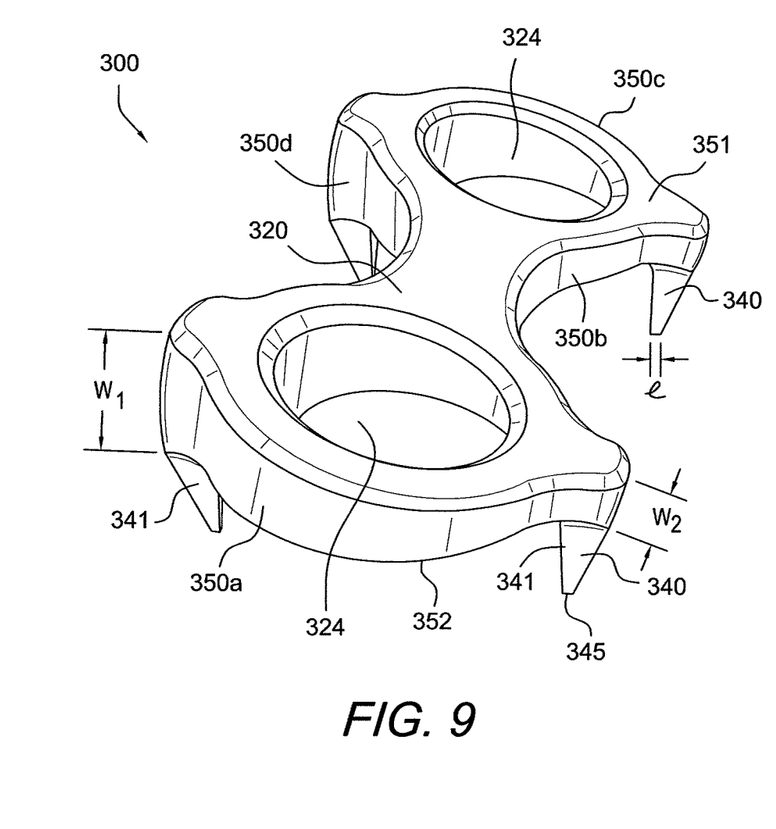
FIG. 9 illustrates a bone plate according to a third embodiment of the present invention.

As shown in FIG. 9, bone plate 300 is provided with a rigid body 320 and four spikes 340 provided symmetrically relative to a longitudinal axis 310 of body 320. Spikes 340 are rigid and, according to an exemplary embodiment only, are provided integral with the body 320. Spikes 340 have a truncated, pyramidal shape with a plurality of sides or faces 341 that converge to tip 345 (line 345) of each spike 340. In an exemplary embodiment only, at least one of the spikes has four lateral faces 341 that converge to tip 345. In a preferred embodiment, all spikes have four lateral faces 341 that converge to tip 345. Tip 345 is preferably a thin line with a length "l" of about 0.1 to 0.2 mm. The height of each spike is of about 3 mm (with the bone plate) or of about 2.5 mm (without the bone plate).

Two openings 324 (that may be threaded) are configured to receive fixation devices (such as, for example, two fixation devices used for the Latarjet procedure). The distance "D" between both holes/threaded openings 324 is preferably of about 10 mm, and more preferably of about 9.5 mm.

Body 320 has a length "L" of about 15 to 20 mm, more preferably of about 18 mm, and a width "W" of about 5 to about 10 mm, more preferably of about 6.5 mm.

As shown in FIG. 9, body 320 of bone plate 300 has a first or top surface 351 and a second or lower surface 352 (which is opposite the first or top surface 351 and which is the bone-contacting surface). Body 320 is also provided with four lateral sides or faces 350a, 350b, 350c and 350d disposed along the perimeter of the second or lower surface 352, and extending about perpendicular to the second or lower surface 352. In an exemplary embodiment, lateral and opposed sides 350a and 350c are similar in that the width "w1" on one side is greater than the width "w2" on the opposite side, with width "w1" gradually decreasing to width "w2" to confer the overall wedged profile to bone plate 300. The special profile of the plate 300 enables orthograde placement of the fixation device (for example, a screw) even in the case of angled bone surfaces.

Bone plate 400 of the fourth embodiment of the present invention (shown in FIG. 10) is similar to the bone plate 300 (shown in FIG. 9) in that bone plate 400 also has a wedged design (as opposed to the parallel design of FIG. 6, for example). However, bone plate 400 is provided with a thicker "FIG. 8" to allow bigger countersinking on the holes, while maintaining the same stability. The special profile and design of the plate 400 enables orthograde placement of the fixation device (for example, a screw) even in the case of angled bone surfaces, and also reduces the overhang of the screw heads.

Figure 10A:
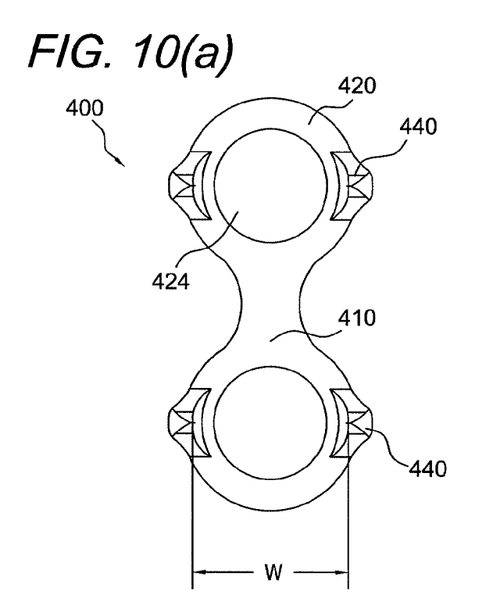
FIG. 10 illustrates a bone plate according to a fourth embodiment of the present invention.
Figures 10B, 10D, 10E, 10F:
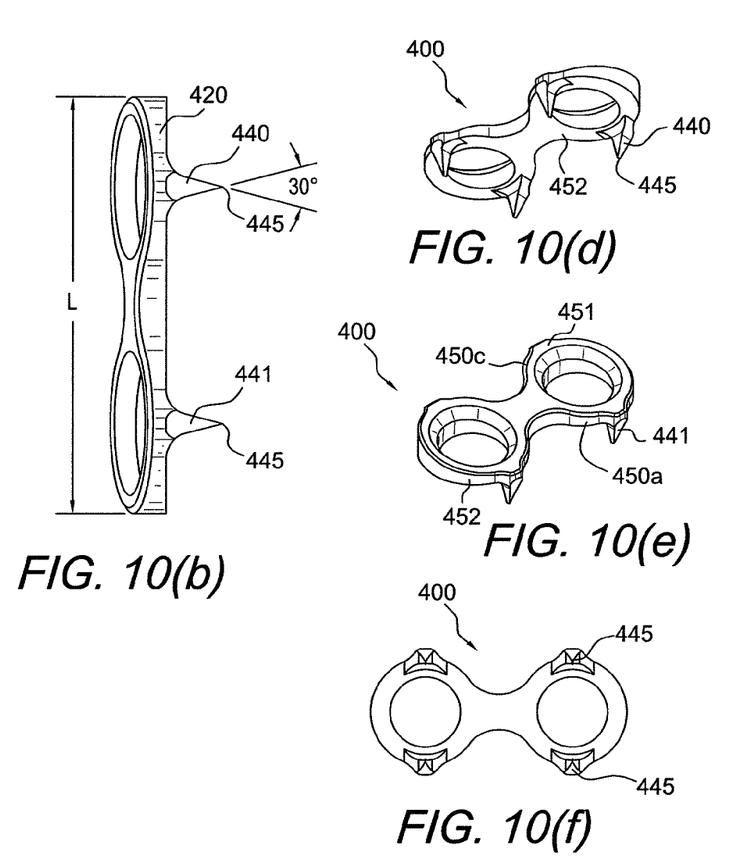

Bone plate 400 is also provided with a rigid body 420 and four spikes 440 provided symmetrically relative to a longitudinal axis 410 of body 420. Spikes 440 are rigid and, according to an exemplary embodiment only, are provided integral with the body 420. Spikes 440 have a truncated, pyramidal shape with a plurality of sides or faces 441 that converge to tip 445 (line 445) of each spike 440. In an exemplary embodiment only, at least one of the spikes has four lateral faces 441 that converge to tip 445. In a preferred embodiment, all spikes have four lateral faces 441 that converge to tip 445. Tip 445 is preferably a thin line with a length "l" of about 0.1 to 0.2 mm. The height of each spike is of about 3 mm (with the bone plate) or of about 2.5 mm (without the bone plate).

Two openings 424 (that may be threaded) are configured to receive fixation devices (such as, for example, two fixation devices used for the Latarjet procedure). The distance "D" between both holes/threaded openings 324 is preferably of about 10 mm, and more preferably of about 9.5 mm.

Body 420 has a length "L" of about 15 to 20 mm, more preferably of about 18 mm, and a width "W" of about 5 to about 10 mm, more preferably of about 6.5 mm.

Figure 10C:
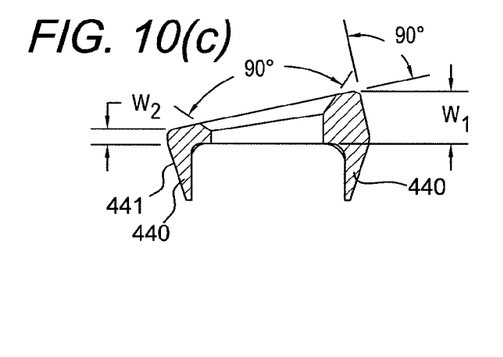

As shown in FIG. 10, body 420 of bone plate 400 has a first or top surface 451 and a second or lower surface 452 (which is opposite the first or top surface 451 and which is the bone-contacting surface). Body 420 is also provided with four lateral sides or faces 450a, 450b, 450c and 450d disposed along the perimeter of the second or lower surface 452, and extending about perpendicular to the second or lower surface 452. In an exemplary embodiment, lateral and opposed sides 450a and 450c are similar in that the width "w1" on one side is greater than the width "w2" on the opposite side, with width "w1" gradually decreasing to width "w2" to confer the overall wedged profile to bone plate 400 (FIG. 10c). In an exemplary embodiment, the difference between w1 and w2 is of about 6 mm. The special profile of the plate 400 enables orthograde placement of the fixation device (for example, a screw) even in the case of angled bone surfaces, and also reduces the overhang of the screw heads.

Bone plate 100, 200, 300, 400 of the present invention is preferably formed of a metal such as titanium, titanium alloy, stainless steel, or other materials that possess mechanical and physical properties suitable for coupling bones together. Preferably, the grain of the metal is oriented parallel with the longer dimension of the bone plate.

Bone plates of the present invention can be provided in various configurations depending on the indicated technique, fusion or osteotomy to be performed. For example, bone plate 100, 200, 300, 400 described above could be employed for internal bone block repairs (such as bone block transplantation using the Latarjet technique or iliac crest bone block transplants) and/or for fusions. In addition, bone plate 100, 200, 300, 400 described above could be employed for knee surgeries, as a tibial anterior/posterior (A/P) sloped osteotomy plate, or as a femoral opening wedge osteotomy plate, among many others. The bone plates of the present invention may be also employed for small joint surgeries.

The bone plates of the present invention may be also fabricated to include additional moveable washers (which may be fully threaded, partially threaded or not threaded), having various diameters and located at various positions on the plate relative to the threaded openings, depending on factors such as the dimensions and particulars of the bones to be coupled, the anatomical configurations of the osteotomy site, or the materials forming the bone plate, among others.

FIGS. 11-22 illustrate an exemplary sequence of steps of a mini open Latarjet procedure conducted with one of the bone plates 100, 200, 300, 400 of the present invention. A skin incision of about 5 cm is made starting at the tip of the coracoid process and extending inferiorly, through the deltoid-to-pectoral approach. Scissors are used to clear the superior aspect of the coracoid process and a retractor (for example, a Hohman retractor) is placed over the top of the coracoid process.

Figure 11:
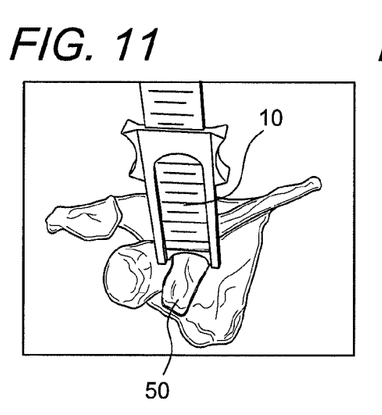
FIGS. 11-22 illustrate a sequence of step of an open Latarjet procedure with a bone plate of the present invention.
Figures 12, 12A:
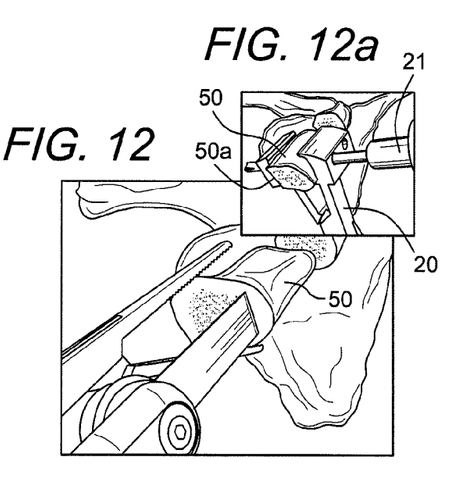

As shown in FIGS. 11 and 12, coracoid graft 50 is resected using a special osteotome 10 or an angled sawblade 10.

In an exemplary embodiment only, the coracoid graft 50 may be additionally shaped and sized (with the same osteotome or with a different cutting instrument, for example) to remove a lateral edge (the spike) and to form a flat, cut surface 50a, as shown in FIG. 12 (for enhanced positioning alongside the glenoid). In this manner, the coracoid graft 50 is positioned so that the cut flat surface 50a abuts the rim of the glenoid.

The coracoid graft 50 is secured within curved inner surfaces of opposing jaws of a grasping drill guide 20 (coracoid guide), as shown in FIG. 12a. Two holes 21a (FIG. 12a) are formed within the graft 50 by engaging drill 21 and by drilling through the clearance slots and through the corresponding holes (guide holes or drill holes) of the jaws of the coracoid guide 20. Holes 21a are formed about parallel within graft 50, and are also formed approximately in the center of the graft. Holes 21a may have various dimensions depending on the graft size and geometry (for example, about two 4 mm holes). In an exemplary embodiment, holes 21a may be formed sequentially; however, the invention is not limited to this embodiment and also contemplates the concurrent formation of holes 21a (as well as the formation of only one hole, depending on the number of cannulations of the offset guide that may be used subsequently).

Figure 13:
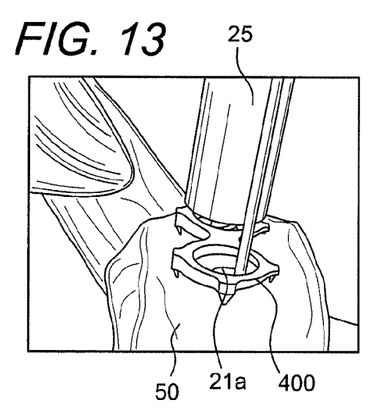

Reference is now made to FIG. 13. A compression cannulated Temporary Compression Device (TCD) 25 is selected (if the 3.75 mm screws are used) to fix one side of the bone plate of the invention (for example, bone plate 400) to the coracoid 50. The thicker part of the plate 400 has to be positioned medial to the glenoid neck.

Figure 14:
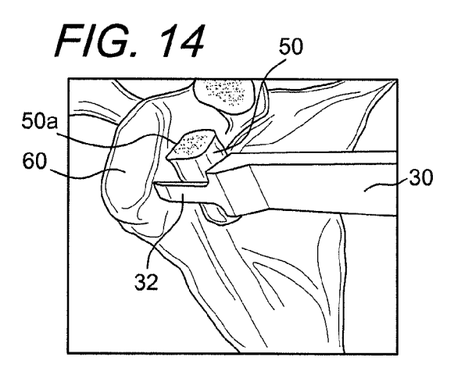

Alternatively, and as shown in FIG. 14, an offset guide 30 (glenoid drillguide 30) with an offset of about 6 or 8 mm may be brought into contact with the coracoid graft 50 (if the 4.0 mm drill is used) to fix the coracoid block 50 on the offset drillguide 30. The coracoid graft 50 (attached to the offset guide 30) is subsequently positioned flush to the rim of glenoid 60 using the center flange 32, as shown in FIG. 14.

Figure 15:
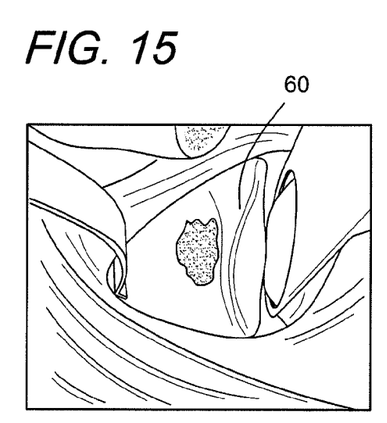

Referring now to FIG. 15, the superior border of the subscapularis is defined. The subscapularis is split and the capsule is open, to expose the anterior glenoid. A retractor (for example, a Gelpi retractor) is used to keep the joint open. Retractors (such as Fukuda, Swan and Blade Retractors) are employed to ensure the access to the antero-inferor part of the glenoid. The glenoid neck may be refreshed with a burr.

Figure 16:
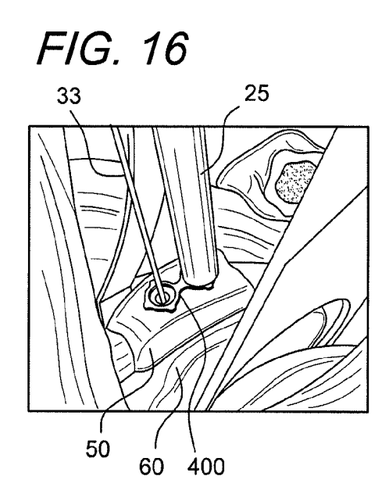

FIG. 16 illustrates the coracoid graft 50 positioned on the prepared glenoid 60 with the TCD 25. Guidewire 33 is drilled through the free hole of the plate 400 into the glenoid 60.

Figure 17:
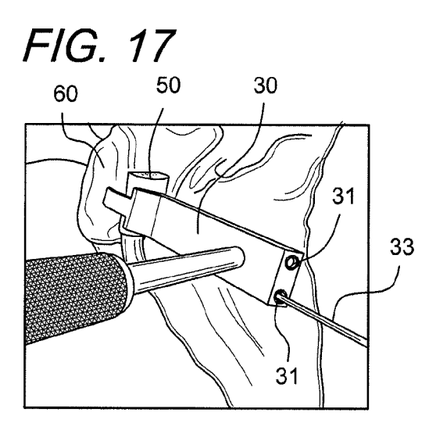

Alternatively, in the technique employing the offset guide 30 (glenoid drillguide 30), and as shown in FIG. 17, the glenoid offset guide 30 (with the coracoid graft 50) is positioned on the glenoid rim. Two parallel guide pins 33 (for example, two 1.5 mm guide pins 33) are the inserted and drilled through cannulations 31 of the offset guide 30 and into the glenoid 60 (preferably conducted with fluoroscopy).

Figure 18:
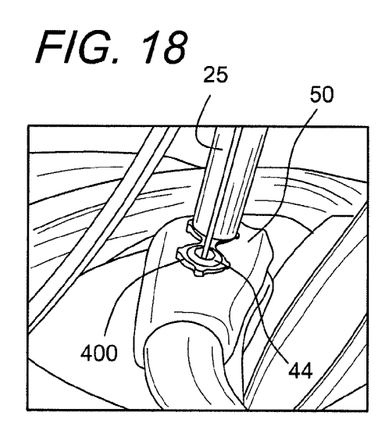

Reference is now made to FIG. 18. TCD 25 is left in position. A first screw 44 is inserted over the guidewire 33 into the plate 400.

Figure 19:
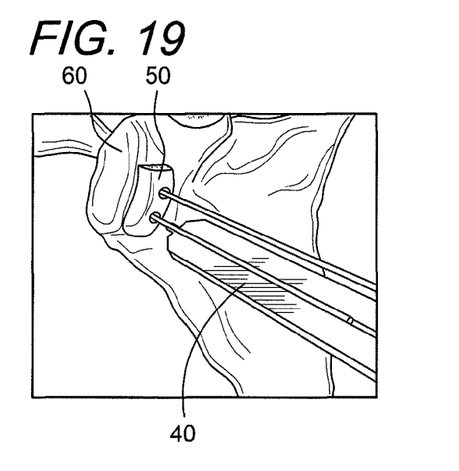

The glenoid offset guide 30 is removed (FIG. 19). The graft 50 may be shaped with a rongeur (for example), if necessary. The length of the screw needed is measured by employing, for example, a depth gauge 40 (FIG. 19) (to determine the optimum screw length, if desired).

Figure 20:
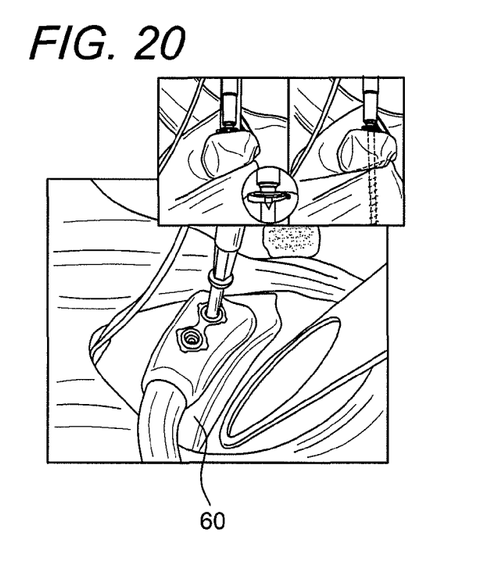

The coracoid graft 50 is positioned properly on the glenoid rim (FIG. 20). The TCD 25 is removed and a second screw 44 is applied over the guidewire 33 (FIG. 20).

Figure 21:
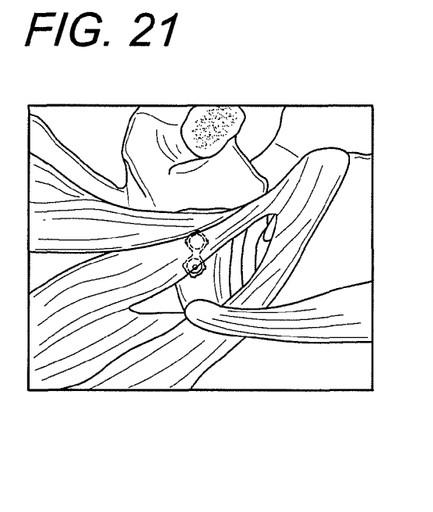

FIG. 21 illustrates the slinging of the conjoined tendon, to give extra stability to the joint. Additional refixation of the labrum may be performed by using additional fixation devices such as suture anchors, for example. If employed, these additional fixation devices could be placed into the glenoid bone beside the graft. The wound may be closed in a layer-by-layer fashion.

Figure 22:
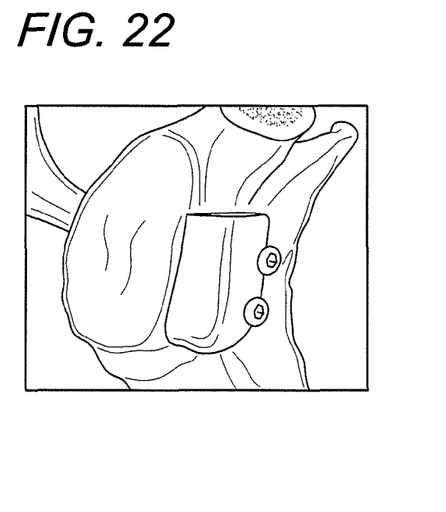

FIG. 22 illustrates the fixation of the bone block achieved by screws only (if no wedged profile plate is used).

Although the present invention has been described above with reference to a specific embodiment (i.e., a coracoid graft attached to the glenoid by employing a bone plate of the present invention), the invention contemplates any attachment of a graft to bone, for example, any allograft or autograft attached to bone, or a graft from the illiac crest, or a tibial or scapular spine graft attached to any bone, among many others, and by employing a bone plate of the present invention.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A bone plate, comprising:
a body having a longitudinal axis, a first surface and a bone-contacting surface opposed to the first surface, and four lateral sides;
a plurality of spikes extending from the bone-contacting surface, each spike having a truncated, pyramidal configuration terminating in a tip line, wherein each spike has four lateral faces or sides that converge to the tip line, and wherein two of the plurality of spikes are positioned on the longitudinal axis and remaining spikes are located opposite each other and in symmetry relative to the longitudinal axis; and two openings extending from the first surface through the body and to the bone-contacting surface, the openings being located on the longitudinal axis of the body, and wherein the plurality of spikes allow easy penetration of bone by pressing the plate with a hand before fixation devices are secured to the bone plate, and wherein two opposed lateral sides of the bone plate have a uniform, gradual width between the first surface and the bone-contacting surface, a first width on one side of the four lateral sides being greater than a second width on a side opposite to the one side of the four lateral sides, the first width gradually decreasing to the second width to confer an overall wedged profile to the bone plate.

2. The bone plate of claim 1, wherein the spikes have a height of about 2.5 to about 3 mm.

3. The bone plate of claim 1, wherein the line has a length of about 0.1 to about 0.2 mm.

4. The bone plate of claim 1, wherein the openings accommodates a screw, an anchor or a washer.

5. The bone plate of claim 1, wherein the spikes extend about perpendicular to the bone-contacting surface.

6. The bone plate of claim 1, wherein the body has a figure-8 configuration.

7. The bone plate of claim 1, wherein the body has an oval configuration.

8. A plate suture assembly for treating a fracture of a bone, comprising:
  a bone plate positioned proximate to the bone, the bone plate comprising:
  a rigid body having a longitudinal axis, a first surface and a bone-contacting surface opposed to the first surface, and four lateral sides;
  a plurality of spikes extending from the bone-contacting surface, each spike having a truncated, pyramidal configuration terminating in a tip line, wherein each spike has four lateral faces or sides that converge to the tip line, the spikes allowing easy penetration of bone by pressing the plate with a hand before fixation devices are secured to the bone plate, wherein two of the plurality of spikes are positioned on the longitudinal axis and remaining spikes are located opposite each other and in symmetry relative to the longitudinal axis; and
  a plurality of openings extending from the first surface through the body and to the bone-contacting surface, the openings being located on the longitudinal axis of the body; and
  at least one fixation device for securing the bone plate to the bone,
  wherein two opposed lateral sides of the bone plate have a non-uniform, gradual width between the first surface and the bone-contacting surface, a first width on one side of the four lateral faces or sides being greater than a second width on a side opposite to the one side of the four lateral faces or sides, the first width gradually decreasing to the second width to confer an overall wedged profile to the bone plate.

9. The plate suture assembly of claim 8, wherein the bone is the coracoid.

10. A bone plate, comprising:
  a body with a wedged profile having a longitudinal axis, a first surface, a bone-contacting surface opposed to the first surface, four lateral sides with at least two side surfaces extending between the first surface and the bone-contacting surface, wherein at least one of the side surfaces has a non-uniform and gradual width between the first surface and the bone-contacting surface, a first width on one side of the four lateral sides being greater than a second width on a side opposite to the one side of the four lateral sides, the first width gradually decreasing to the second width to confer the wedged profile to the bone plate; and
  a plurality of spikes having a truncated, pyramidal configuration terminating in a tip line and extending from the bone-contacting surface, the spikes allowing easy penetration of bone by pressing the plate with a hand before fixation devices are secured to the bone plate, wherein two of the plurality of spikes are positioned on the longitudinal axis and remaining spikes are located opposite each other and in symmetry relative to the longitudinal axis.

11. The bone plate of claim 10, wherein two side surfaces have a non-uniform width.

12. The bone plate of claim 11, wherein each of the two side surfaces has a gradual width.

13. The bone plate of claim 12, wherein each of the two side surfaces has a width that gradually increases from about 2 mm to about 3.5 mm.

14. The bone plate of claim 10, wherein the spikes have a height of about 2.5 to about 3 mm.

15. The bone plate of claim 10, wherein the tip line has a length of about 0.1 to about 0.2 mm.

16. The bone plate of claim 10, wherein each spike has four lateral faces converging to the line.

17. The bone plate of claim 10, further comprising at least one aperture passing through the plate.

18. The bone plate of claim 17, wherein the aperture accommodates a screw, an anchor or a washer.

19. The bone plate of claim 10, wherein the spikes extend about perpendicular to the bone-contacting surface.

20. The bone plate of claim 10, wherein the body has a figure-8 configuration.

21. A method of treating a fracture of a bone, comprising the steps of:
  providing a bone plate with a wedged profile having a body with a longitudinal axis, a first surface, a second surface opposed to the first surface, four lateral side surfaces with at least two side surfaces extending between the first surface and the second surface, wherein each of the side surfaces has a non-uniform and gradual width between the first surface and the second surface opposed to the first surface, a first width on one side of the four lateral side surfaces being greater than a second width on a side opposite to the one side of the four lateral side surfaces, the first width gradually decreasing to the second width to confer the wedged profile to the bone plate; and a plurality of spikes extending from one of the first or second surface;
  positioning the bone plate proximal to a fracture of a bone;
  pressing the bone plate against the bone so that the spikes enter the bone, the spikes allowing easy penetration of bone by pressing the plate with a hand before fixation devices are secured to the bone plate, wherein two of the plurality of spikes are positioned on the longitudinal axis and remaining spikes are located opposite each other and in symmetry relative to the longitudinal axis; and
  subsequently, securing the bone plate to the bone.

22. The method of claim 21, wherein the step of securing the bone plate to the bone further comprises the steps of:
  providing at least one through-hole through the bone plate; and
  securing a fixation device through the through-hole and into the bone.

23. The method of claim 22, wherein the fixation device is selected from the group consisting of a washer, a screw and an anchor.

24. The method of claim 21, wherein, each spike has a pyramidal configuration terminating in a line.

25. The method of claim 21, wherein, each spike has a pyramidal configuration terminating in a point.

26. The method of claim 21, wherein the bone is the coracoid and the method is a Latarjet procedure.

* * * * *